US012738381B2

(12) United States Patent
Zhi et al.

(10) Patent No.: US 12,738,381 B2
(45) **Date of Patent: *Sep. 15, 2026**

(54) MACHINE LEARNING FRAMEWORK FOR DETECTION OF CHRONIC HEALTH CONDITIONS

(71) Applicant: Aetna Inc., Hartford, CT (US)

(72) Inventors: Naiqian Zhi, Hartford, CT (US); Sarah Wohlman, Hartford, CT (US); Alex Xu, Hartford, CT (US); Ryan Berns, Hartford, CT (US); Rajiv Bhan, Hartford, CT (US); Sumeet Kumar, Hartford, CT (US); Alan Leggitt, Hartford, CT (US); Li Qin, Hartford, CT (US)

(73) Assignee: Aetna Inc., Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/947,650

(22) Filed: Nov. 14, 2024

(65) Prior Publication Data

US 2025/0069753 A1 Feb. 27, 2025

Related U.S. Application Data

(63) Continuation of application No. 17/692,109, filed on Mar. 10, 2022, now Pat. No. 12,176,109.

(51) Int. Cl.
*G16H 50/20* (2018.01)
*G06N 3/044* (2023.01)
(Continued)

(52) U.S. Cl.
CPC ............. *G16H 50/20* (2018.01); *G06N 3/044* (2023.01); *G06N 3/045* (2023.01); *G16H 10/65* (2018.01)

(58) Field of Classification Search
CPC ........ G16H 50/20; G16H 10/65; G06N 3/045; G06N 3/044
See application file for complete search history.

(56) References Cited

U.S. PATENT DOCUMENTS

| | | | | |
|---|---|---|---|---|
| 11,100,289 | B1 * | 8/2021 | Kailasam | G06F 40/30 |
| 11,830,623 | B1 * | 11/2023 | Aranke | G16H 50/70 |

(Continued)

OTHER PUBLICATIONS

T. Wang, Y. Tian and R. G. Qiu, "Long Short-Term Memory Recurrent Neural Networks for Multiple Diseases Risk Prediction by Leveraging Longitudinal Medical Records," in IEEE Journal of Biomedical and Health Informatics, vol. 24, No. 8, pp. 2337-2346, Aug. 2020 (Year: 2020).*

(Continued)

*Primary Examiner* — Matthew L Hamilton
(74) *Attorney, Agent, or Firm* — Leydig, Voit & Mayer, Ltd.

(57) ABSTRACT

A system and method are disclosed for detecting chronic health conditions based on data collected by a wearable device such as an activity tracker or a smart watch. Deep learning algorithms are configured to process the monitored parameter data collected by the wearable device as well as additional embedding data obtained from health records corresponding to a user account registered to the wearable device. In some examples, the input vector can also include embedding data related to social determinants data and/or demographic data. The output of the deep learning algorithms provides predictions that represent probabilities that the user of the wearable device has an underlying health condition. If any underlying health condition is detected, then the user can be notified directly, via the wearable device or an associated application or technology, or indirectly, via a primary care provider associated with the user.

20 Claims, 9 Drawing Sheets

(51) Int. Cl.
*G06N 3/045* (2023.01)
*G16H 10/65* (2018.01)

(56) References Cited

U.S. PATENT DOCUMENTS

| | | | | |
|---|---|---|---|---|
| 2017/0132395 | A1 | 5/2017 | Futch | |
| 2018/0232495 | A1 | 8/2018 | Li et al. | |
| 2019/0096525 | A1* | 3/2019 | Ferenc | G16H 50/20 |
| 2019/0198174 | A1 | 6/2019 | Abbaspour et al. | |
| 2020/0075152 | A1 | 3/2020 | Radovcic | |
| 2020/0138360 | A1 | 5/2020 | Fan et al. | |
| 2020/0155078 | A1* | 5/2020 | Mei | A61B 5/7267 |
| 2020/0185073 | A1 | 6/2020 | De Brouwer | |
| 2020/0202997 | A1 | 6/2020 | Hadad et al. | |
| 2021/0296000 | A1* | 9/2021 | Shaw | G06Q 30/0202 |
| 2021/0407667 | A1 | 12/2021 | Zhi et al. | |
| 2022/0254493 | A1* | 8/2022 | Wu | G16H 50/70 |
| 2022/0284277 | A1 | 9/2022 | Zhu et al. | |
| 2023/0248320 | A1* | 8/2023 | Lafon | A61B 5/742<br>600/549 |

OTHER PUBLICATIONS

Mikolov et al., "Efficient Estimation of Word Representations in Vector Space," ICLR Workshop Papers (2013).

Aqeel, A., Hassan, A., Khan, M. A., Rehman, S., Tariq, U., Kadry, S., . . . Thinnukool, O. (2022). A long short-term memory biomarker-based prediction framework for Alzheimer's disease. (Year: 2022).

Zhao, J., QiPing, F., Wu, P., Lupu, R. A., Wilke, R. A., Wells, Q. S., . . . Wei-Qi, W. (2019). Learning from longitudinal data in electronic health record and genetic data to improve cardiovascular event prediction. Scientific Reports (Nature Publisher Group), (Year: 2019).

* cited by examiner

MACHINE LEARNING FRAMEWORK FOR DETECTION OF CHRONIC HEALTH CONDITIONS

CROSS-REFERENCE TO RELATED APPLICATIONS

This patent application claims the benefit of U.S. patent application Ser. No. 17/692,109, filed Mar. 10, 2022, which is incorporated by reference herein.

TECHNICAL FIELD

The application relates to machine learning. More specifically, the application is directed to a machine learning framework for detection of chronic health conditions.

BACKGROUND

Wearable health monitoring systems such as the features built into consumer devices like a Fitbit® device or an Apple® Watch, among others, or clinical devices like network connected blood glucose monitors are becoming more common. Consumers are tracking their steps (e.g., pedometer), heart rate (e.g., resting heart rate, peak heart rate, heart rate variability, etc.), oxygen level (e.g., VO2 Max), activity levels (e.g., calories, minutes of exercise, etc.), and the like using these devices, typically to encourage a more active and healthy lifestyle. This data generates thousands or millions of data points for a consumer, and some of this information can be highly correlated to the presence of certain diseases, oftentimes undiagnosed. However, this data is typically not shared with a patient's primary care physician or used in any clinical setting for medical diagnosis.

Some of the consumer companies have developed application programming interfaces (APIs) that allow this data to be shared with third parties, such as a clinician or a company offering health-based incentives such as discounts for those individuals that meet certain goals. In some cases, certain parameters like heart rate or VO2 max can be tracked over time and analyzed by artificial intelligence algorithms to attempt to detect certain health conditions. However, such algorithms are typically limited as they are not tailored to a specific user's physiology. The effectiveness of the artificial intelligence algorithm might not be sufficient for a user to rely on the output of said algorithm. Therefore, there is a need to improve the algorithms directed to use this wearable activity tracker data.

SUMMARY

A system and method for detecting chronic health conditions are disclosed. Deep learning techniques are utilized to analyze monitored parameter data collected by a wearable device in conjunction with additional embedding data derived from health records or other sources. In particular, the techniques and systems described herein can be utilized by insurance providers or other sources of health record information to supplement the monitored parameter data collected by the wearable device.

In accordance with a first aspect of the present disclosure, a system for detecting chronic health conditions is disclosed. The system includes a server device including a memory and one or more processors. The one or more processors are configured to: receive monitored parameter data corresponding to data points collected over a number of days from a wearable device; process the monitored parameter data by a convolution neural network (CNN) to generate a feature map; divide the feature map into a plurality of tensors, each tensor corresponding to a different day in the number of days; process the tensors by a long short-term memory (LSTM) network to generate an embedding vector for the monitored parameter data; combine the embedding vector for the monitored parameter data with one or more additional embedding vectors to generate an input vector; and process the input vector by artificial intelligence algorithm to generate an output vector that indicates a prediction related to a plurality of health conditions for a user of the wearable device.

In an example of the first aspect, the wearable device is an activity tracker. The monitored parameter data includes data points related to one or more of: a heart rate; an oxygen level; an activity level including at least one of a number of steps, a number of flights climbed, or a duration of exercise; or a number of calories burned.

In an example of the first aspect, the monitored parameter data further includes information logged by a user manually.

In an example of the first aspect, the one or more additional embedding vectors includes a first embedding vector obtained by processing health records for a user via a natural language processing algorithm. The health records correspond to a registered user of the wearable device.

In an example of the first aspect, the health records are stored in a database and comprise at least one of: claims records received from a health care provider; prescription records received from a pharmacy; or laboratory results received from a laboratory or other health care provider.

In an example of the first aspect, the one or more additional embedding vectors further includes a second embedding vector related to social determinants data including one or more of: economic information; neighborhood information; education information; nutritional information; or other environmental information.

In an example of the first aspect, the second embedding vector is further related to demographic data including one or more of: age information; gender information; neighborhood type information; family size information; or employment indicator information.

In an example of the first aspect, the artificial intelligence algorithm comprises one or more of: a multi-layer perceptron (MLP) algorithm; a convolution neural network (CNN); or a recurrent neural network (RNN).

In an example of the first aspect, the artificial intelligence algorithm comprises a number of convolutional layers and a plurality of fully connected layers. Each fully connected layer corresponds to a different health condition in the plurality of health conditions.

In an example of the first aspect, the one or more processors are further configured to transmit a notification message to one of the wearable device or a mobile device associated with the wearable device to provide a user of the wearable device with a suggested action based on the prediction.

In accordance with a second aspect of the present disclosure, a method for detecting chronic health conditions is disclosed. The method includes the steps of: receiving monitored parameter data corresponding to data points collected over a number of days from a wearable device; processing the monitored parameter data by a convolution neural network (CNN) to generate a feature map; dividing the feature map into a plurality of tensors, each tensor corresponding to a different day in the number of days; processing the tensors by a long short-term memory (LSTM) network to generate an embedding vector for the monitored parameter data; combining the embedding vector for the monitored parameter data with one or more additional embedding vectors to generate an input vector; and processing the input vector by artificial intelligence algorithm to generate an output vector that indicates a prediction related to a plurality of health conditions for a user of the wearable device.

In an example of the second aspect, the wearable device is an activity tracker. The monitored parameter data includes data points related to one or more of: a heart rate; an oxygen level; an activity level including at least one of a number of steps, a number of flights climbed, or a duration of exercise; or a number of calories burned.

In an example of the second aspect, the one or more additional embedding vectors includes a first embedding vector obtained by processing health records for a user via a natural language processing algorithm. The health records correspond to a registered user of the wearable device.

In an example of the second aspect, the health records are stored in a database and comprise at least one of: claims records received from a health provider; prescription records received from a pharmacy; or laboratory results received from a laboratory or other health provider.

In an example of the second aspect, the one or more additional embedding vectors further includes a second embedding vector related to social determinants data including one or more of: economic information; neighborhood information; education information; nutritional information; or other environmental information.

In an example, wherein the artificial intelligence algorithm comprises a number of convolutional layers and a plurality of fully connected layers, each fully connected layer corresponding to a different health condition in the plurality of health conditions.

In an example of the second aspect, the method further includes transmitting a notification message to the wearable device to provide a user of the wearable device with a suggested action based on the prediction. In an example, the notification message is transmitted to a healthcare provider to suggest treatment options that may be applicable to a patient.

In accordance with a third aspect of the present disclosure, a non-transitory computer-readable medium is provided for storing instructions that, responsive to being executed by one or more processors of a computing device, cause the computing device to perform the method of the second aspect.

DETAILED DESCRIPTION

Figure 1A:
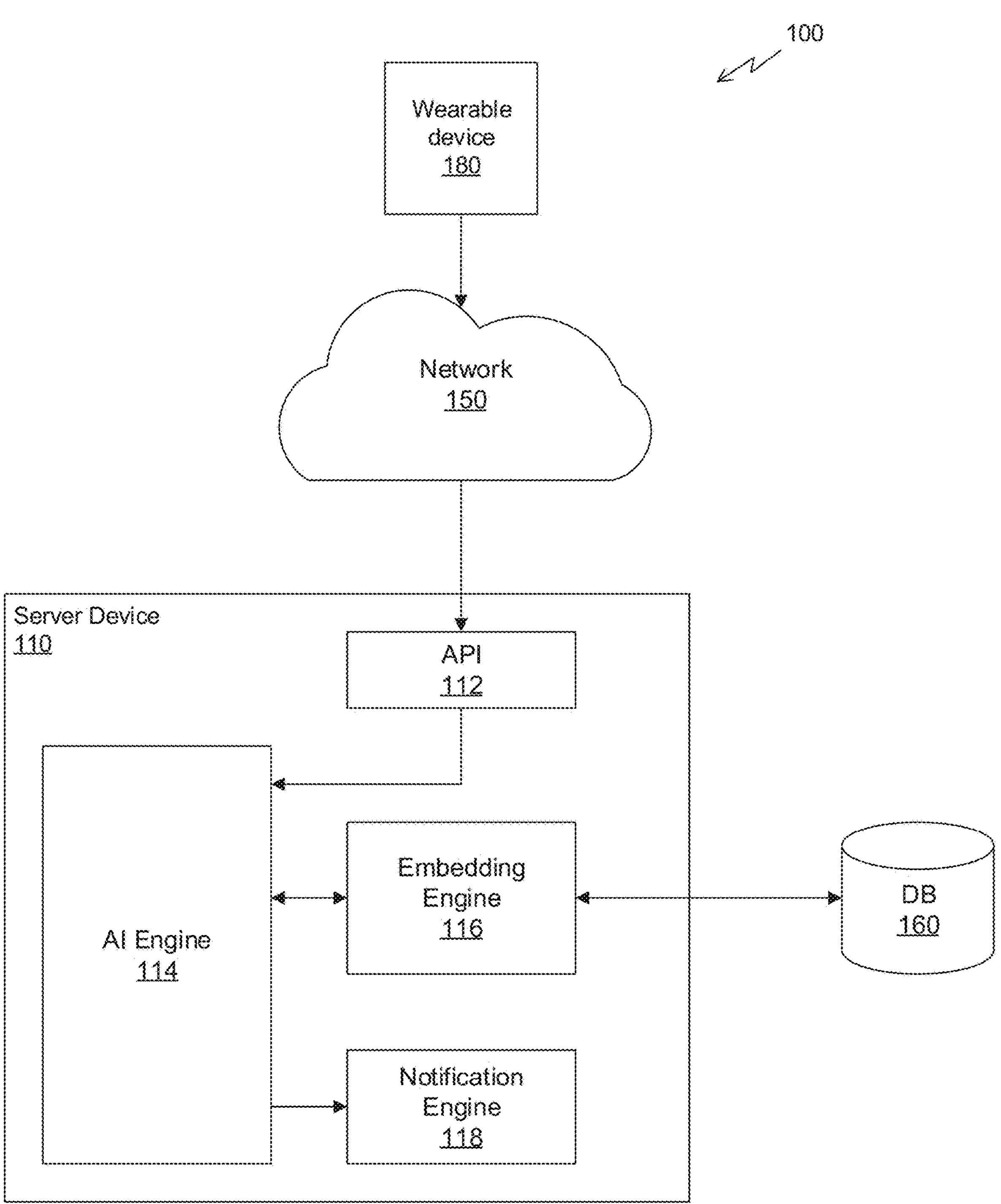
FIG. 1A illustrates a system for monitoring health conditions, in accordance with some examples.

Artificial Intelligence (AI) and Deep Learning Neural Networks (DLNN) can be utilized to assist in detecting chronic health conditions such as, but not limited to, obesity, diabetes, sleep apnea, depression, pre-depression, hypertension, hyperlipidemia, and cardiovascular disease. A wearable device, such as a wearable activity tracker, oximeter, blood glucose monitor, or the like, can provide one or more monitored parameters to a server device. The monitored parameters can include, but are not limited to, a heart rate, heart rate variability, an electro cardiogram (ECG), a blood oxygen level, blood pressure, a duration of exercise, a number of steps, an altitude, exposure to environmental parameters (e.g., audio signals, air quality, temperature, etc.), menstruation cycles (e.g., basal body temperature, etc.), sleep cycles, acceleration (e.g., fall detection), nutrition information, and the like. The parameters can be logged automatically via sensor input or manually via user input, or any combination thereof. In some examples, the wearable device can be paired with other devices (e.g., blood glucose monitor, etc.) to collect parameter data. The monitored parameters can provide data points collected periodically, such as every second, minute, hour, or day. Different parameters can be collected at different frequencies. For example, a heart rate may be collected every minute whereas a heart rate variability can be collected daily (e.g., as derived from a plurality of heart rate data points collected throughout a 24 hour period).

A user registers the wearable device with a user account. The user account can be associated with additional data that can be used to supplement the monitored parameter data from the wearable device. For example, the additional data can include claims data for an insured person that is maintained by an insurance provider, which can include data collected from the insured person's primary care physician, clinical labs, pharmacies, or other health providers that submit claims information to the insurance provider for payment and/or processing. The claims data provides the insurance provider with additional insight into the health history of the patient. The additional data can also include data collected from surveys, screeners, or other questions presented to the user (e.g., surveys related to nutrition, diet, social determinants information, medical conditions, mental health conditions, etc.) and data collected from a user's personal device, such as a cell phone or other mobile device (e.g., data regarding a user's cell phone usage, including the amount of time a user spends playing games, on social media, accessing apps, texting, participating in phone calls, etc., a user's number of contacts, number of phone calls, number of texts, etc.).

While the wearable device provides the AI algorithm with limited health information in a real-time or near real-time basis, the data is typically limited in scope and only provides insight into a small number of parameters related to a user's health. In contrast, the claims information may provide much more detailed insight into a specific user's physiology, but is typically collected on a much more limited basis (e.g., during once or twice a year appointments, when a person fills a prescription, when labs are run, etc.). By combining this data to provide a broad range of information to an AI algorithm, much more accurate assessments can be made by the AI algorithm, providing a user with more insight into potential health concerns before the person might otherwise be aware of the symptoms of such conditions.

FIG. 1A illustrates a system 100 for monitoring health conditions, in accordance with some examples. As depicted in FIG. 1A, the system 100 includes a server device 110 connected to a network 150. The server device 110 comprises a memory and one or more processors configured to execute instructions. In an example, the server device 110 is a blade server included in a chassis on a rack of a data center. In another example, the server device 110 is a virtual machine that is run in the cloud. Although the components shown in the server device 110 can be executed by a single processor, in other examples, the server device 110 can refer to two or more server devices, each component included in the server device 110 executed by a particular one or more of the two or more server devices. For example, in an example, the AI engine 114 can be executed on a second server device that is implemented in a public cloud such as Amazon® Web Services or Microsoft® Azure. The API 112, embedding engine 116, and/or notification engine 118 can be implemented on a private server device hosted in a data center operated by an insurance provider and can be configured to communicate with the AI engine 114 over a network. It will be understood that reference to a single server device 110 can include reference to multiple server devices.

In some examples, the server device 110 includes an application programming interface (API) 112, an artificial intelligence (AI) engine 114, an embedding engine 116, and a notification engine 118. The API 112 implements a set of algorithms to process API calls from a client. In an example, the API 112 is configured to receive data packets that include the API calls from a wearable device 180. The API calls can include monitored parameter data collected by the wearable device 180. As used herein, the term "monitored parameter data" refers to one or more data points (e.g., samples) of each of one or more monitored parameters such as, but not limited to, a heart rate, heart rate variability, and ECG, an oxygen level, an activity level including at least one of a number of steps, a number of flights climbed, or a duration of exercise, a number of calories burned, a basal body temperature, a sleep duration, a blood glucose level, or the like. For example, the wearable device 180 can include light sensors that, when placed proximate a user's skin, are used to monitor a user's heart rate or blood oxygen level. As another example, the wearable device 180 can include a temperature sensor placed proximate the user's skin, that measures a surface temperature of the user's body at the location of the temperature sensor. The wearable device 180 collects one or more data points over a period of time such as a day or week, and then the wearable device 180 generates an API call including the data points and transmits the API call to the server device 110 via the network 150.

In some examples, the network 150 is a wide area network (WAN) such as the Internet. In other examples, the network 150 can be a radio access network such as a $4^{th}$ Generation (LTE, 4G) or Next Generation (5G) cellular network. In yet other examples, the network 150 can be a local area network (LAN) or a personal area network (PAN). The data packets can be Internet Protocol (IP) packets. It will be appreciated that any network, wired or wireless, can be utilized to transmit monitored parameter data to the server device 110 using any technically feasible protocols.

In some examples, the API 112 pre-processes the monitored parameter data received from the wearable device 180 and transmits the processed monitored parameter data to the AI engine 114. For example, the heart rate data can represent a number of data points, and the API 112 can be configured to derive average daily heart rate data from the monitored parameter data. In an example, the API 112 can be configured to filter the monitored parameter data to select only a subset of parameters that are applicable for a given AI algorithm. For example, the monitored parameter data can include heart rate data, step information, calorie information, and oxygen level information. A particular AI algorithm may only call for heart rate data and oxygen level information and, therefore, the API 112 is configured to discard the step information and calorie information.

In some examples, the API 112 is configured to anonymize the monitored parameter data. Information related to a user's health is a privacy concern and, therefore, the API 112 can take steps to ensure any personally identifying information (PII) is removed before the monitored parameter data is forwarded to the AI engine 114. It will be appreciated that the API 112 may need to associate the monitored parameter data with a particular user or device, such as by using an identifier included in the API call or the header of a data packet to correlate the wearable device 180 with a particular user. The identifier can be a user identifier (ID) that is assigned to the wearable device 180 when the user registers the wearable device with a health monitoring service, or the identifier can be a network address, such as a media access control (MAC) address or an IP address of the wearable device 180. In some examples, the API 112 can use the identifier to allocate a task ID with the monitored parameter data such that the AI engine 114 or any other process that accesses the data cannot directly correlate the data with a particular user, user account, or user ID. In some cases, the monitored parameter data is also encrypted, either by the wearable device 180 or by the API 112.

In other examples, the API 112 stores the monitored parameter data in a memory or database, and sends a request message to the AI engine 114 that indicates the monitored parameter data is available at the memory or the database. It will be appreciated that the API 112 facilitates the collection of monitored parameter data from one or more wearable devices 180 associated with one or more distinct users or user accounts and provides the AI engine 114 with the monitored parameter data for processing.

In some examples, the AI engine 114 is configured to process inputs with one or more AI algorithms. The AI algorithms can include, but are not limited to, a multi-layer perceptron (MLP) algorithm, a convolution neural network (CNN), or a recurrent neural network (RNN). The AI algorithm uses the monitored parameter data to generate outputs that represent predictions related to the health of a user. For example, a CNN may be utilized to process an input vector including a number of data points that represent a heart rate variability for a user over a number of days (e.g., 7 days, 30 days, etc.). The heart rate variability data can be shown to be indicative of certain underlying health conditions such as hypertension, hyperlipidemia, sleep apnea, diabetes, and cardiovascular disease. The use of certain monitored parameter data collected from a wearable device and analyzed by deep learning models may be useful in helping to diagnose people with undetected conditions, but the accuracy of such models is not perfect because each individual has a unique physiology and environment. The heart rate of a young healthy individual with low body fat when compared against the heart rate of an older obese individual can be very different, even though the young person may be diabetic and the older person may not have any detected condition. Therefore, the AI algorithms can be improved by augmenting the monitored parameter data collected by the wearable device with additional information related to the user.

In an example, the AI engine 114, upon receiving the monitored parameter data from the API 112, generates a request that is transmitted to the embedding engine 116. The request can include an identifier associated with the wearable device 180. The embedding engine 116 is configured to collect health records or other information from one or more data stores such as a database 160. For example, a health insurance provider can receive claims data from a variety of health care providers. The claims data is stored in a database 160 and used to process insurance claims. However, the embedding engine 116 can query the database 160 for any health records related to a user using the identifier included in the request. Thus, the embedding engine 116 collects additional information from one or more sources that is not available to the wearable device 180.

In some examples, the embedding engine 116 is configured to collect the additional information that is combined with the monitored parameter data from the wearable device 180 to increase the information provided as an input to the AI algorithm. In one example, a health insurance provider receives data related to a user's health as well as general demographic information and/or social determinants information. The data can include claims records received from a health provider, prescription records received from a pharmacy, or laboratory results received from a laboratory or other health care provider. The claims information may contain information about specific medical procedures undergone by the user in the past. The laboratory results can contain detailed information related to a user's comprehensive metabolic panels, for example. The prescription records can include information about the types of medications taken by a user. All of this information can provide a more comprehensive picture of the user's health condition than could be provided by the monitored parameter data alone.

In an example, the embedding engine 116 is configured to process health records for a user via a natural language processing algorithm. Again, the health records correspond to a registered user of the wearable device. It will be appreciated that the health records that are retrieved from the database 160 can have a variety of formats. For example, a claims record may include a set of fields, each field including different information such as a member identifier, insurance product information, medical codes (e.g., ICD9 diagnostic codes), and the like. The job of the embedding engine 116 is to take a number of different natural language or standardized format health records and generate a vector of dimensionless features (e.g., 100 features) that indicates a user's health history over a specified time period. For example, a particular dimension can represent a particular combination of medical codes found throughout the user's health records. This feature vector, generated by a natural language processing algorithm such as Word2vec described in Mikolov et al., "Efficient Estimation of Word Representations in Vector Space," ICLR Workshop Papers, 2013, which is herein incorporated in its entirety, or the like, represents the additional data that is combined with the monitored parameter data.

For example, a member's health history includes a sequence of medical codes including ICD (International Statistical Classification of Diseases) 9/10 diagnostic codes, CPT (Current Procedural Terminology) procedure codes, GPI (Generic Product Identifier) drug codes, and LOINC (Logical Observation Identifiers Names and Codes) lab codes. The embedding engine 116 includes a 100-dimensional lookup matrix that is trained based on health histories of millions of members collected over a number of years. The health history of a particular member can be parsed to extract the codes set forth above, to generate a list of codes included in that member's health history. Each code is then processed by the lookup matrix to generate a corresponding 100-dimensional vector and the average of the vectors for the set of codes generated from the member's health history is provided as the embedding data.

In some examples, the embedding data is combined with additional data such as demographic data (e.g., age, race, gender, etc.) or social determinants data, described in more detail below. When combined with the monitored parameter data, this information provides a more comprehensive view of the user's health that can be processed by the AI algorithm.

The AI engine 114 processes the input vector(s) via one or more AI algorithms. In some examples, the AI engine 114 can generate separate input vectors for each AI algorithm, according to the requirements of the AI algorithm. For example, one type of algorithm can be better for diagnosing a medical condition such as hypertension while a different type of algorithm can be better for diagnosing a medical condition such as sleep apnea. The output vector from each of the one or more AI algorithms can represent classifiers associated with different medical conditions. A classifier can be a scalar value between 0 and 1 that represents a probability that the user may have the underlying health condition associated with that classifier.

Once the output vector(s) are generated, the AI engine 114 may compare each classifier to a threshold value. If the classifier is above a threshold value, then the user may have a high likelihood of having the underlying health condition. In such cases, the AI engine 114 can transmit a request to the notification engine to notify the user about the detected health condition.

In an example, the notification engine 118 can generate a notification message that is transmitted to the wearable device 180 to provide a user of the wearable device with a suggested action. For example, the suggested action can include information to facilitate scheduling an appointment with a healthcare provider. In another example, the notification message is transmitted to a healthcare provider to suggest treatment options that may be applicable to a patient (e.g., the user).

Figure 1B:
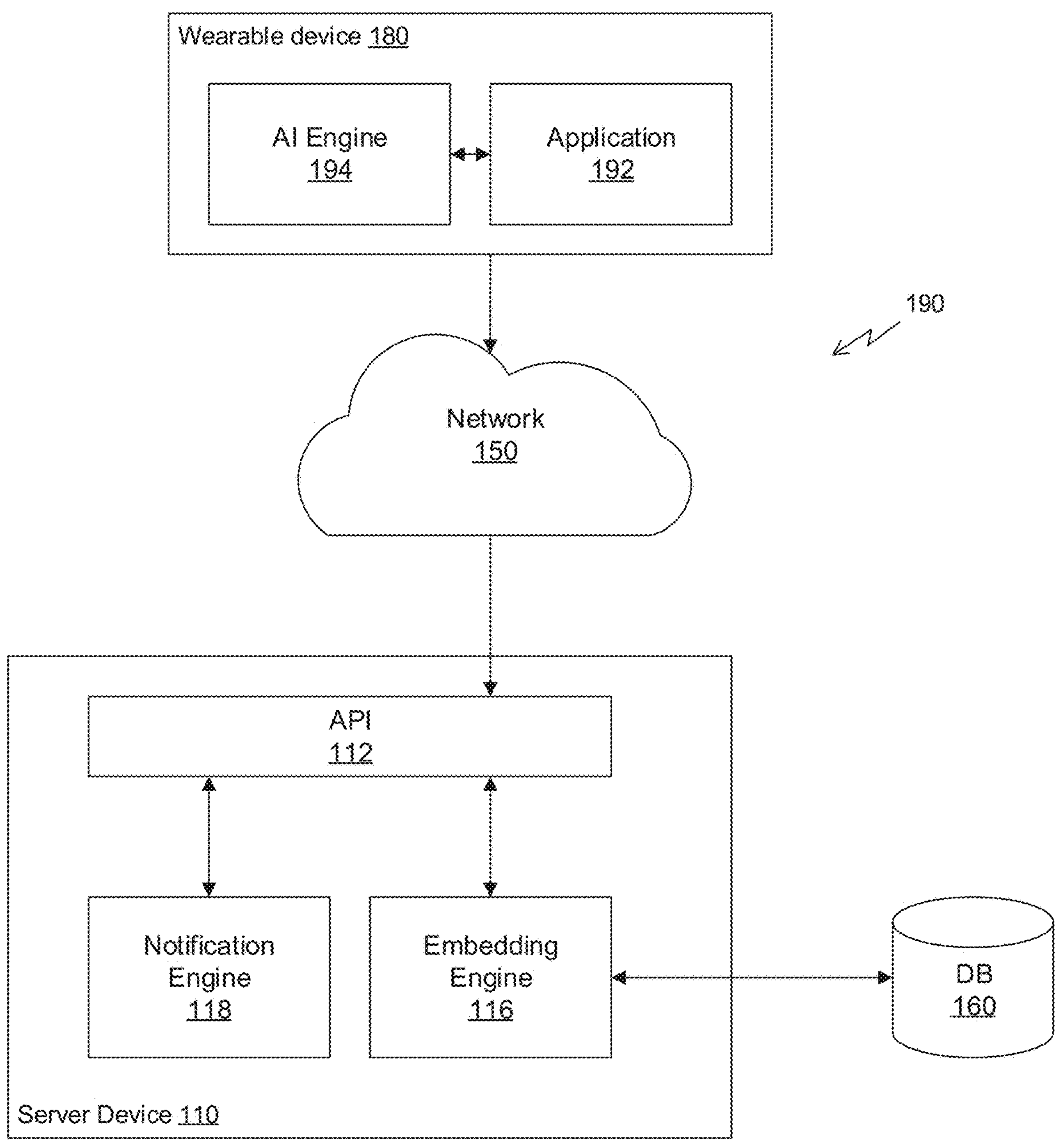
FIG. 1B illustrates a system for monitoring health conditions, in accordance with other examples.

FIG. 1B illustrates a system 100 for monitoring health conditions, in accordance with other examples. As depicted in FIG. 1B, the wearable device 180 includes an application 192 configured to collect data points on one or more parameters monitored by the wearable device 180. In addition, the wearable device 180 also includes the AI engine 194, which is similar to AI engine 114 but is executed locally on the wearable device 180. Rather than transmitting the parameter data collected by the wearable device 180 to the sever device 110, the application 192 can request the server device 110 to transmit embedding data generated by the embedding engine 116 to the application 192, which combines the embedding data with the monitored parameter data stored on the wearable device 180. The combined data is then processed by the AI engine 194 to generate the output vector(s) as described above.

It will be appreciated that the system 190 may be more secure than the system 100 as the monitored parameter data is not transmitted over the network 150, and the embedding data transmitted over the network 150 is merely a vector that represents a user's health history and is not easily translated into the original health history information stored in the database 160. However, the system 190 may require more computing capacity in the wearable device 180 in order to execute the AI algorithm(s).

In some examples, the functionality of the wearable device 180 can be split between a wearable activity tracker with limited processing capacity and a mobile device, such as a cellular phone or tablet computer. The mobile device can be connected to the network 150 and the wearable activity tracker can be connected to the mobile device. An application on the mobile device collects monitored parameter data from the wearable activity tracker and transmits the monitored parameter data to the server device 110 to be processed by the AI engine 114, as in system 100, or receives embedding data from the server device 110 to be processed by the AI engine 194, as in system 190. In other examples, the mobile device can be used to provide the wearable device 180 with at least some monitored parameter data. For example, a user can use the mobile device to provide manually logged data related to one or more monitored parameters that are sent to the wearable activity tracker for processing. In such examples, the mobile device can provide additional user interfaces for the wearable activity tracker, but the wearable activity tracker maintains the functionality for processing the monitored parameter data.

Figure 2A:
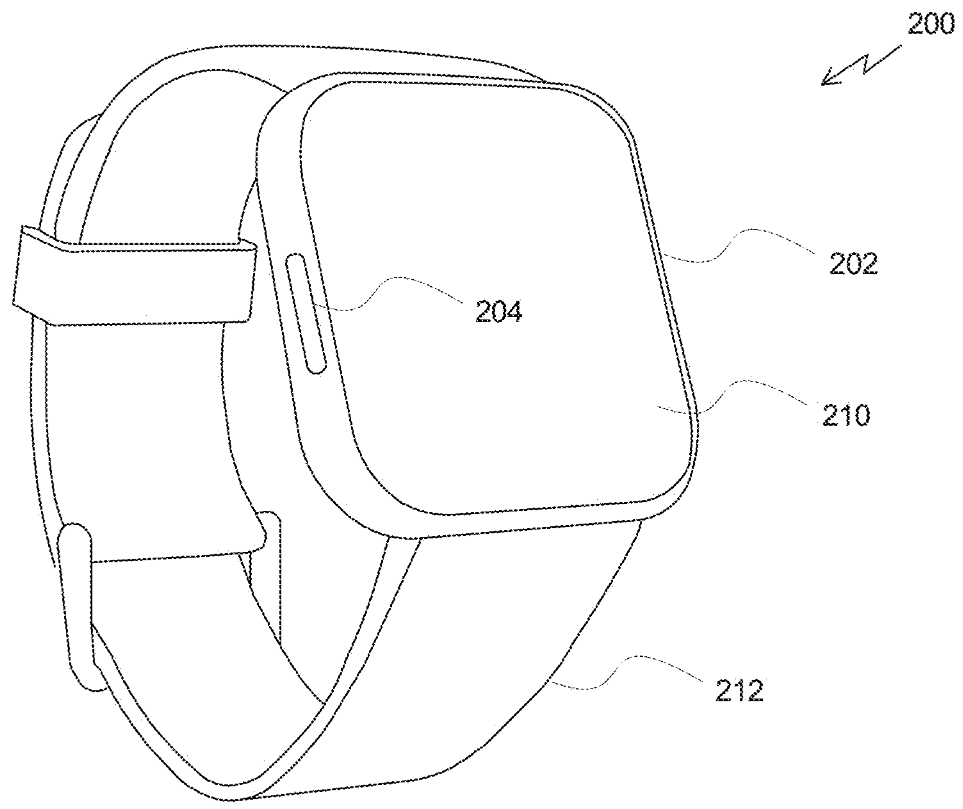
FIGS. 2A & 2B illustrate a wearable device, in accordance with some examples.
Figure 2B:
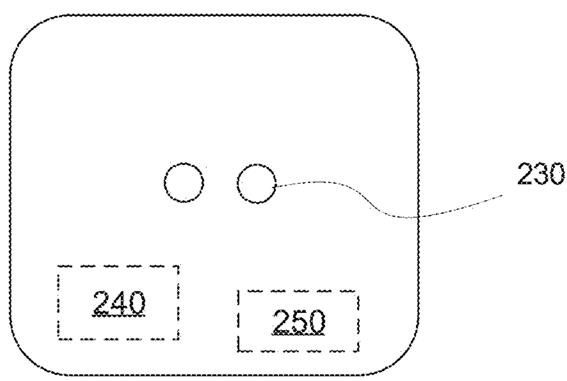

FIGS. 2A & 2B illustrate a wearable device 200, in accordance with some examples. The wearable device 200 is a watch that includes sensors for collecting data points on one or more parameters related to the health of a user. As shown in FIG. 2A, the wearable device 200 includes a body 202 that houses electronics including a processor, a memory, a transceiver, an antenna, a battery, and the like. The wearable device 200 also includes a button 204, a display 210, and a band 212. The display 210 is a liquid crystal display (LCD), an organic light emitting diode (OLED) display, or the like. The display 210 is configured to display information to a user and can include a touch function that enables the user to enter information using the wearable device. The display 210 can display information such as a time or date, notifications such as alarms or indications of a text message or phone call, and information related to collected information such as a number of steps counted in a day using a pedometer function or a current heart rate of the user, among other information.

As shown in FIG. 2B, the back of the body 202 can include sensors 230 for collecting monitored parameter data. For example, the sensors 230 can include a light emitting diode that produces a light and a light sensor that detects lights (e.g., optical pulse sensors). The light emitted from the light emitting diode can enter the user's skin and the signal detected by the light sensor can be used to monitor, for example, a user's heart rate or blood oxygen level. The sensors 230 can include other types of sensors such as capacitive sensors, moisture sensors, image sensors, electrooculogram (EOG) or electroretinogram (ERG) sensors, respiration sensors, airflow sensors, temperature sensors, and the like. The scope of the present disclosure is not limited to a specific type of sensor and any sensor capable of collecting any kind of health information about a user is contemplated as being included in the wearable device 200.

As depicted in FIG. 2B, the wearable device 200 includes a processor 240 and a transceiver 250. In some examples, the processor 240 is a system on chip (SoC) and is configured to execute one or more processes that collect monitored parameter data using the sensors 230 and transmit the monitored parameter data to the server device 110 via the transceiver. In one example, the wearable device 200 is configured to transmit the monitored parameter data to an access point connected to a network using Wi-Fi or some other wireless technology.

It will be appreciated that the wearable device 200 shown in FIGS. 2A & 2B is only one exemplary device and that other types of wearable devices are contemplated as being within the scope of this disclosure. For example, the wearable device 200 could be a clinical medical device such as a blood glucose monitor or a wearable electrocardiogram (ECG) monitor, smart glasses that include augmented reality and/or virtual reality capabilities, smart rings, bracelets, headbands, hearing aids, or any other devices worn by a user that include one or more sensors for monitoring some parameter related to the user. In some examples, the wearable device is a smart phone that includes a fitness application that tracks, e.g., an activity level of a user.

Figure 3:
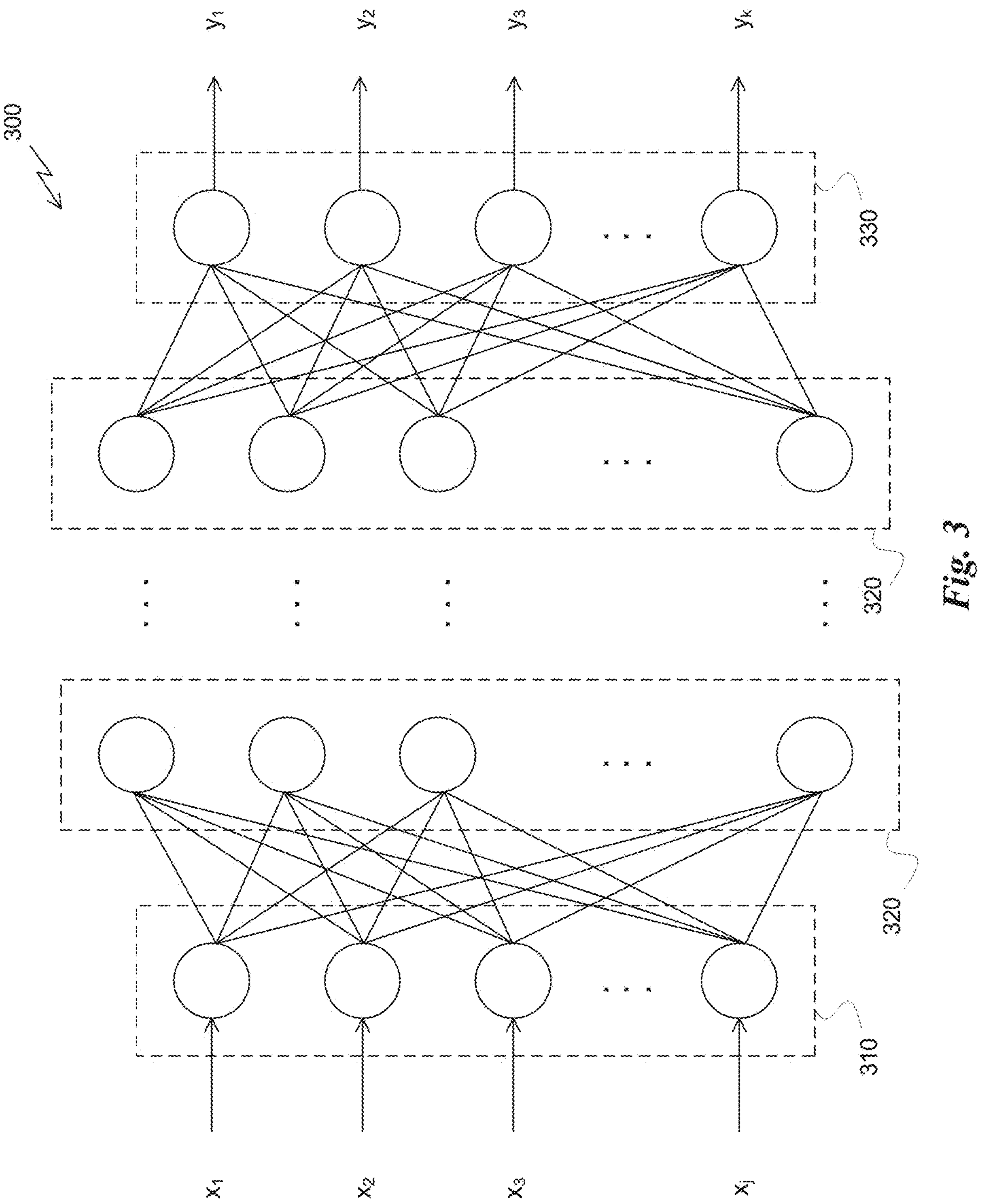
FIG. 3 is an artificial intelligence algorithm, in accordance with some examples.

FIG. 3 is an artificial intelligence algorithm 300, in accordance with some examples. The AI algorithm 300 is a multi-layer perceptron (MLP) algorithm. The MLP is a neural network that includes a plurality of artificial neurons arranged in a series of layers. As depicted in FIG. 3, the MLP includes an input layer 310, one or more hidden layers 320, and an output layer 330. Each artificial neuron within a layer is connected to one or more artificial neurons in a subsequent layer, but no artificial neuron in a particular layer is connected to another artificial neuron in the particular layer.

An input vector, $\{x_1, x_2, \ldots, x_j\}$, is provided as inputs to the input layer 310, where each element of the input vector is coupled to one of the artificial neurons in the input layer 310. Each artificial neuron applies a linear transformation and, optionally, a nonlinear transformation to the inputs connected to the artificial neuron. In the linear transformation, a weight can be applied to each of one or more inputs attached to the artificial neuron and then the weighted inputs can be summed to produce an intermediate output signal. In the nonlinear transformation, the intermediate output signal can be processed by an activation function such as a Sigmoid function or a Rectified Linear Unit (ReLU) to produce an activation signal of the artificial neuron. The activation signal can be fanned out to one or more artificial neurons in the subsequent layer.

The input layer 310 is followed by one or more hidden layers 320. The number of artificial neurons in the hidden layer 320 does not have to match the number of artificial neurons in the input layer 310. In some examples, each hidden layer is fully connected, meaning that each artificial neuron in the hidden layer receives all of the activation signals generated by the set of artificial neurons in the previous layer (e.g., the input layer or a preceding hidden layer). In other examples, each artificial neuron in the hidden layer receives only a subset of activation signals generated by the set of artificial neurons in the previous layer.

The output layer 330 follows the last hidden layer 320 and generates an output vector, $\{y_1, y_2, \ldots, y_k\}$. It will be appreciated that the dimension j of the input vector can be independent of the dimension k of the output vector. In an example, each element of the output vector represents a probability of a person associated with the input vector having a particular underlying medical condition.

In an example, the input vector is composed of a first portion corresponding to monitored parameter data from a wearable device 180 and a second portion corresponding to embedding data associated with a user registered to the wearable device 180. In some examples, the input vector can also include additional information such as demographic data and/or social determinants data, as discussed in more detail below.

It will be appreciated that the AI algorithm 300 is trained using a training data set. In an example, a health insurance company collects data related to a large number of insured individuals. The data can include both health records and monitored parameter data from wearable devices. The health records provide insight on subpopulations in the number of insured individuals that have been diagnosed with one of a variety of medical conditions. The health records can be analyzed to create a ground-truth output vector for each individual. The health records and monitored parameter data collected from a wearable device registered to that individual can be used to generate an input vector that corresponds to the ground-truth output vector. Pairs of input vectors and ground-truth output vectors can then be stored in a database for a large number of insured individuals to generate the training data set.

In order to train the AI algorithm 300, various parameters of the AI algorithm 300 are initialized. In an example, each artificial neuron is associated with a set of weights corresponding to the inputs connected to the artificial neuron. Each weight can be initialized to a random or pseudo-random value (e.g., each weight can be set between 0 and 1, or −1 and 1). In some examples, each artificial neuron can also be associated with a bias value. Once the parameters of the AI algorithm 300 are initialized, each input vector in the training data set is processed by the AI algorithm 300 to generate an output vector. The output vector is compared to the ground-truth output vector for that individual based on a cost function, and the parameters of the AI algorithm 300 are adjusted using known techniques, such as back propagation with gradient descent, in order to minimize the cost function. The cost function can be an L1 cost function such as a sum of absolute differences (SAD) or an L2 cost function such as a sum of square differences (SSD).

Once the AI algorithm 300 is trained, the AI algorithm 300 can be employed with new user data. As monitored parameter data is received from a wearable device 180, the input vector can be generated, including the corresponding embedding data, and processed to generate an output vector. The output vector classifies the probability that the user may have one of a plurality of undiagnosed medical conditions.

As described above, the MLP is only one type of AI algorithm 300 that can be implemented by the AI engine 114. The MLP is applied to a one dimensional input vector having a number of elements. In contrast, other AI algorithms 300 can be implemented that analyze a two dimensional input vector.

Figure 4:
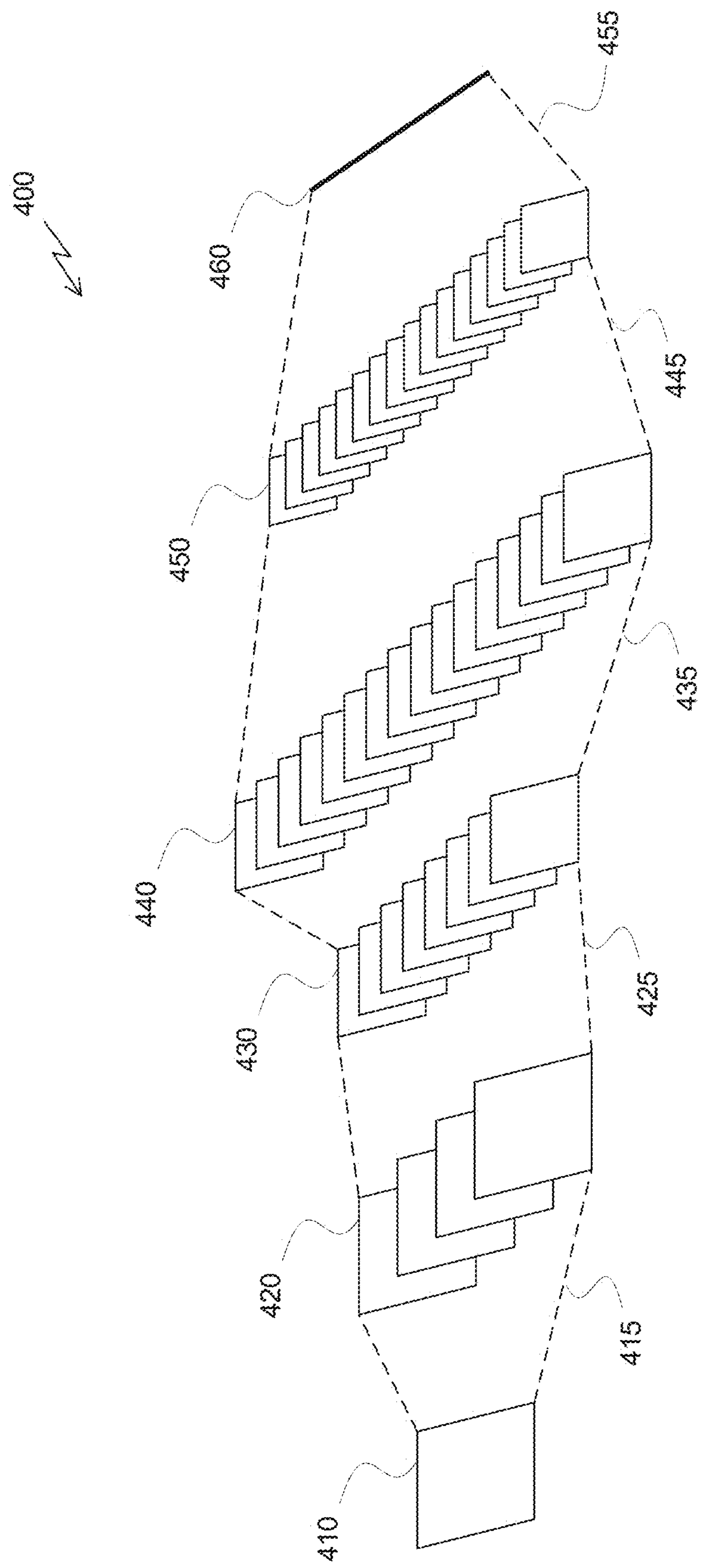
FIG. 4 illustrates a convolution neural network (CNN), in accordance with some examples.

FIG. 4 illustrates a convolution neural network (CNN) 400, in accordance with some examples. A CNN is typically used in applications such as image classification or image processing. The convolution operation applies a moving filter, referred to as a convolution kernel, across the input image to generate a set of feature maps. Each layer of the CNN further refines the set of feature maps through subsequent convolution operations and downsampling in order to generate a large number of features that are significantly reduced in spatial resolution. A fully connected layer then combines these features to generate an output vector. In some examples, CNNs can be implemented as U-nets, which include an encoder portion that generates the set of features and a decoder portion which performs deconvolution operations and upsampling to generate a processed image from the set of features generate by the encoder portion.

As depicted in FIG. 4, an input vector 410 is a two-dimensional matrix. A first portion of the matrix comprises monitored parameter data. A second portion of the matrix comprises embedding data. In some examples, the matrix can also include demographic data and/or social determinants data. In some examples, the input vector is a plurality of channels, each channel including a two dimensional matrix. A first channel includes the monitored parameter data, a second channel includes the embedding data, and, optionally, a third channel and/or a fourth channel includes demographic data and social determinants data, respectively.

A first layer 415 of the CNN 400 performs a two dimensional convolution operation on the input vector 410 to generate a set of feature maps 420. The number of channels of the feature maps can be more than the number of channels of the input vector 410. For example, each channel of the feature maps 420 can correspond to a different convolution kernel applied to a particular channel of the input vector 410.

A second layer 425 is a downsampling layer that generates a second set of feature maps 430 from the set of feature maps 420. The downsampling operation can be implemented by a pooling layer or, less typically, a convolution operation with a stride greater than one element. A stride refers to moving the convolution filter by more than one element each time the convolution filter is applied to the input feature map. For example, a stride of 2×2 means that the convolution filter is applied to every other element of the feature map such that the output feature map is half the resolution of the input feature map in each dimension. A pooling layer, on the other hand, is applied to a subset of elements (e.g., each 2×2 set of elements) and selects, either, a maximum value in the subset, a mean value in the subset, or a minimum value in the subset as the output for a corresponding element in the output feature map. It will be appreciated that the number of channels in the feature maps output by a pooling layer is typically the same as the number of channels in the feature maps input to the pooling layer. However, where subsampling is implemented using convolution operations with strides greater than one in either dimension, the number of channels in the feature maps can increase.

The CNN 400 can include additional layers such as a convolution layer 435 and a subsampling layer 445 that generate sets of feature maps 440 and 450, respectively. Although not shown explicitly, a large number of layers can be included in the CNN 400. Examples of deep neural networks can include more than 50 or 100 layers. Furthermore, although not shown explicitly, the CNN 400 can also include activation layers, which apply an activation function to each of the elements of the feature maps. Again, examples of common activation functions are RcLU and Sigmoid.

The final layer 455 is a fully connected layer that processed the set of feature maps 450 to generate an output vector 460. In one example, the output vector 460 is a one-dimensional vector that classifies the probability of an individual to have each of a plurality of undetected medical conditions. In other examples, the output vector 460 can be a two-dimensional matrix.

It will be appreciated that the AI algorithm is not limited to the MLP or the CNN implementations described above. In another example, the AI algorithm is a recurrent neural network (RNN). In an example, the RNN is implemented similar to the MLP of FIG. 3, except each neural network maintains a state h that can affect the activation level of the artificial neuron. Essentially, a recurrent neural network is similar to the MLP except that the past state of each neuron is not returned to a base state before processing a new input vector. In another example, the RNN is implemented similar to the CNN of FIG. 4, where the fully connected layer 455 is replaced with one or more recurrent layers (e.g., bidirectional layers) that maintain a state h.

Other types of AI algorithms are also within the scope of the present disclosure. These algorithms can include residual neural networks, regression algorithms, and the like. The particular type of AI algorithm that is implemented can depend on the particular application and may consider the particular type of monitored parameter data received from a wearable device 180.

Figure 5:
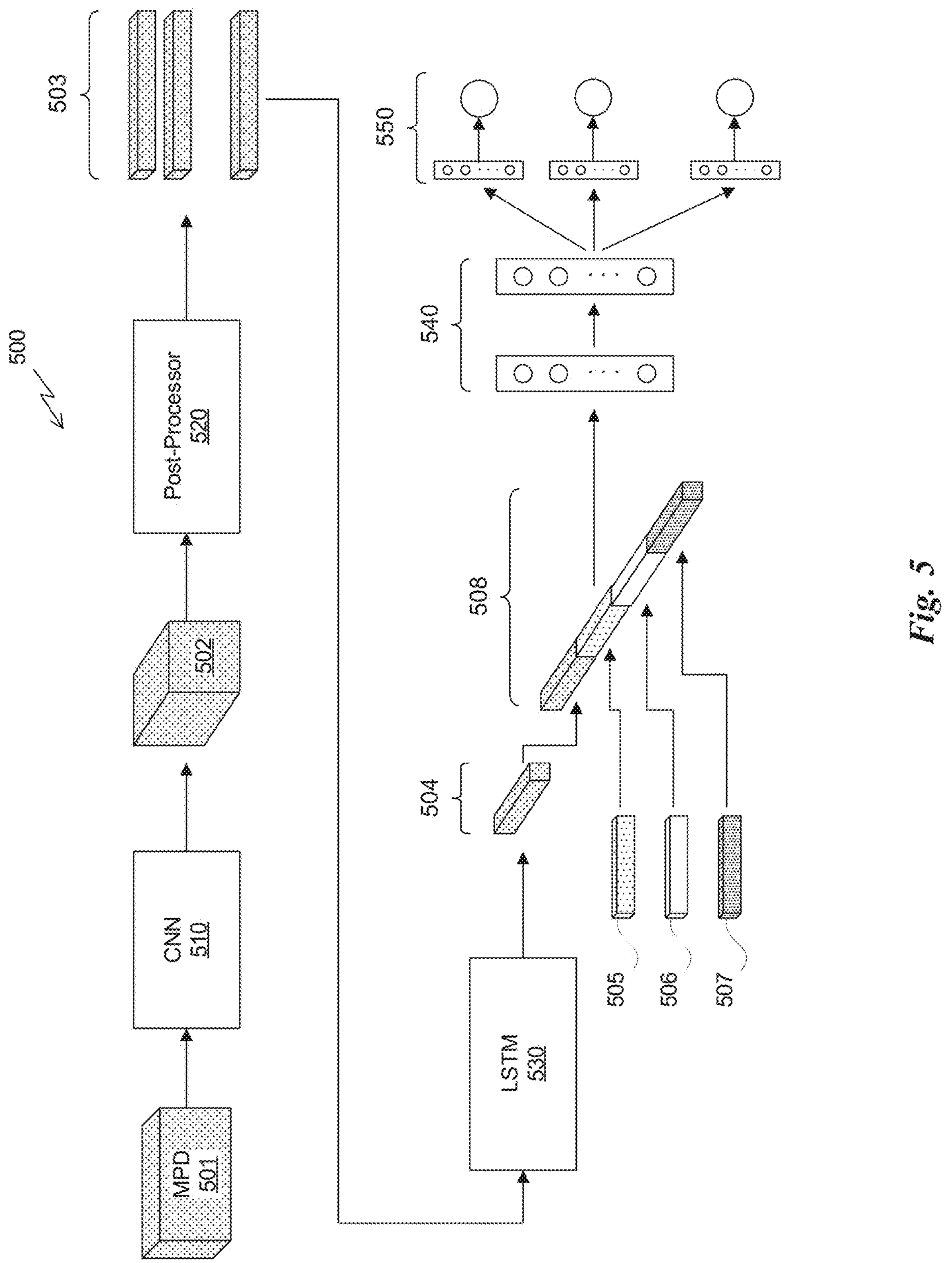
FIG. 5 illustrates a machine learning framework for detecting chronic health conditions, in accordance with some examples.

FIG. 5 illustrates a machine learning framework 500 for detecting chronic health conditions, in accordance with some examples. The framework 500 is configured to process monitored parameter data 501 collected by a wearable device 180. In an example, the monitored parameter data 501 includes samples for up to 25 channels collected over 7 days, each channel representing a different parameter. Of course, the number of parameters and the number of days samples that are collected can vary from the examples described herein.

In an example, the monitored parameter data 501 is processed separately by a CNN 510. The CNN 510 includes a number of one-dimensional convolutional layers that are configured to process the monitored parameter data 501. The CNN 510 generates a feature map 502 that may identify patterns in the monitored parameter data. The feature map 502 can have different dimensions than the monitored parameter data 501. For example, feature vectors in the feature map 502 may correspond to two or more parameters (channels) in the monitored parameter data 501. Each feature may comprise a vector having a number of elements (e.g., 128 elements). Thus, the feature map 502 may be, for example, of size 21×7×128 corresponding to 21 128-element vectors over each of 7 days.

In an example, the feature map 502 is then processed by a post-processor module 520, which is configured to reshape the features into a two-dimensional tensor 503, where the first dimension corresponds to the number of input days. In an example, the output of the post-processor module 520 comprises a tensor 503 corresponding to the seven days of monitored parameter data 501.

The tensor 503 is then processed by a long-short term memory (LSTM) network 530. The LSTM 530 is a type of recurrent neural network that includes recurrent feedback connections inside the network such that the output from one input depends on the sequence of previous inputs. In an example, the LSTM 530 processes the tensor 503 to recognize patterns in the features of the monitored parameter data 501 over the seven day period. The LSTM 530 then generates a one-dimensional vector that represents a feature 504 of the monitored parameter data 501. The feature 504 is then combined with embedding data 505 related to health records, embedding data 506 related to demographic and/or social determinants data, and/or embedding data 507 related to search term data to generate an input vector 508. The embedding data 507 related to search term data can represent a vector corresponding to a user's previous interactions with a search engine. For example, the embedding data 507 may represent an insured individual searching for a specific type of provider (e.g. a physical therapist), using a web page or mobile application hosted by an insurance provider.

The combined input vector 508 can then be processed by another machine learning model 540, such as the MLP 300 or a CNN 400, described above. In an example, the machine learning model 540 includes a number of convolutional layers that generate a feature representation of the input vector 508. The feature representation is then processed by separate and distinct fully connected layers 550 corresponding to each of a plurality of different health conditions. The fully connected layers 550 generate a scalar output that represents a probability that the user has a particular health condition. For example, a first fully connected layer 550 predicts whether the user is likely to have diabetes and a second fully connected layer 550 predicts whether the user is likely to have hypertension. A plurality of different fully connected layers 550 can be defined for a number of different health conditions.

In an example, the ML framework 500 can be trained based on a loss function corresponding to a cross entropy parameter, a recall parameter and/or a precision parameter. The cross entropy parameter is a widely used measure of the total difference between two probability distributions, in this case the true labels (whether or not an individual has the underlying disease) and the predicted probability generated by the model. The recall parameter is a measure of how many individuals with a condition are correctly predicted to have that condition by the model. In other words, recall is essentially a measurement of false negatives. The precision parameter is a measure of how many individuals that are predicted to have a condition by the model actually have the condition. In other words, precision is essentially a measurement of false positives. In an example, the threshold used to identify a positive or negative result can be tuned in order to align with a stated goal for outreach.

In an example, the ML framework 500 can be adapted for different subsets of users. In a first adaptation, users with a short patient history (e.g., users that are new to the service and/or have very little established health records), which may be referred to as short tenure users, can be processed using a subset of the embedding vectors as the input to the AI algorithm 540. In an example, only the embedding vector for the monitored parameter data 504 and the embedding vector 506 related to demographic information are utilized in the input vector 508, omitting the embedding data 505 related to health records and the embedding data 507 relating to search term data. In contrast, utilizing a second adaptation of the framework 500, users with a longer patient history (e.g., users that have at least 6 months of established health records), which may be referred to as long tenure users, can be processed using all of the embedding vectors 504-507, or any other combination thereof. In some examples, different instances of the ML framework 500 can be trained separately based on different training data sets.

Figure 6:
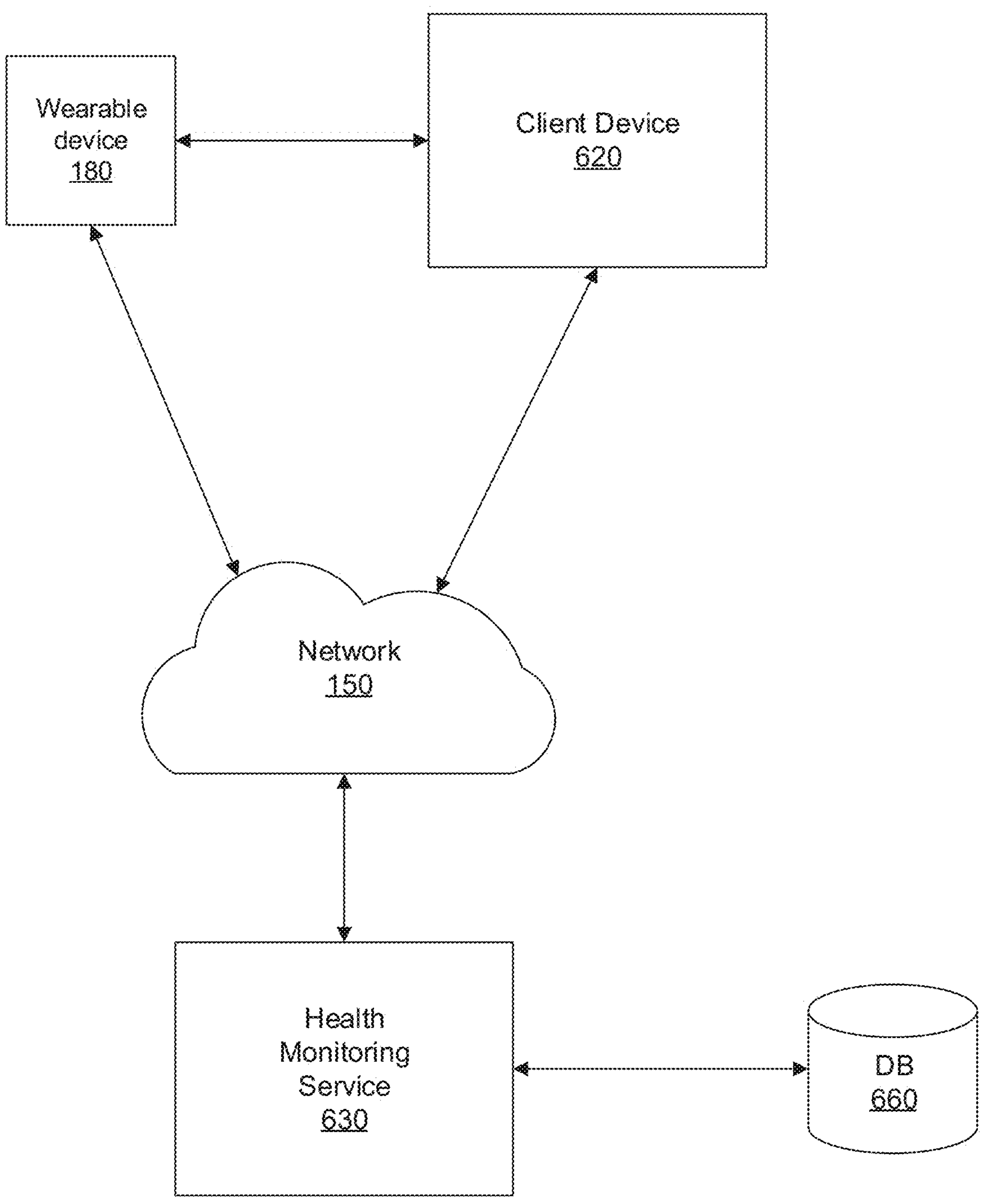
FIG. 6 is a conceptual illustration of a health monitoring service for identifying medical conditions based on monitored parameter data collected by a wearable device, in accordance with some examples.

FIG. 6 is a conceptual illustration of a health monitoring service 630 for detecting chronic health conditions, in accordance with some examples. When a user obtains a wearable device 180, the user can opt-in to use a health monitoring service 630 offered by a service provider. In an example, the user, through a client device 610, can access a web page using a web browser or other application executed by the client device 610. In an example, the web page is a portal for an insurance provider and the user is prompted to log into a user account using credentials established by the user for a user account. Once logged in, the user may select an option provided through the web page to register a wearable device with the account and opt-in to a health monitoring service 630.

In one example, the user provides information to identify the wearable device to the health monitoring service 630. For example, the user can enter a MAC address of the wearable device in a form element provided on the webpage. In another example, the health monitoring service 630 can prompt the user to download an application on the wearable device, where the application is configured to communicate directly with the health monitoring service 630. Once the application is running on the wearable device 630, the user can enter credentials for the user account in the application on the wearable device 180 or, alternatively, the user can be provided with a temporary code at the client device 610, which the user can then enter in the application on the wearable device 180. The temporary code is then transmitted from the wearable device 180 to the health monitoring service 630, which can then associate an identifier corresponding to the wearable device 180 with the user account based on the temporary code.

The example examples described above are merely a few of the many possible ways to register the wearable device 180 to the user account for the user. Any means for registering the wearable device 180 to the user account is contemplated as being within the scope of the present disclosure. Once the wearable device 180 is registered to the user account, such as by mapping a user account identifier to an identifier for the wearable device 180 in a database 660, the monitored parameter data received from the wearable device 180 can be associated with health records corresponding to the user account in order to generate the embedding data utilized, at least in part, by the AI algorithm.

Figure 7:
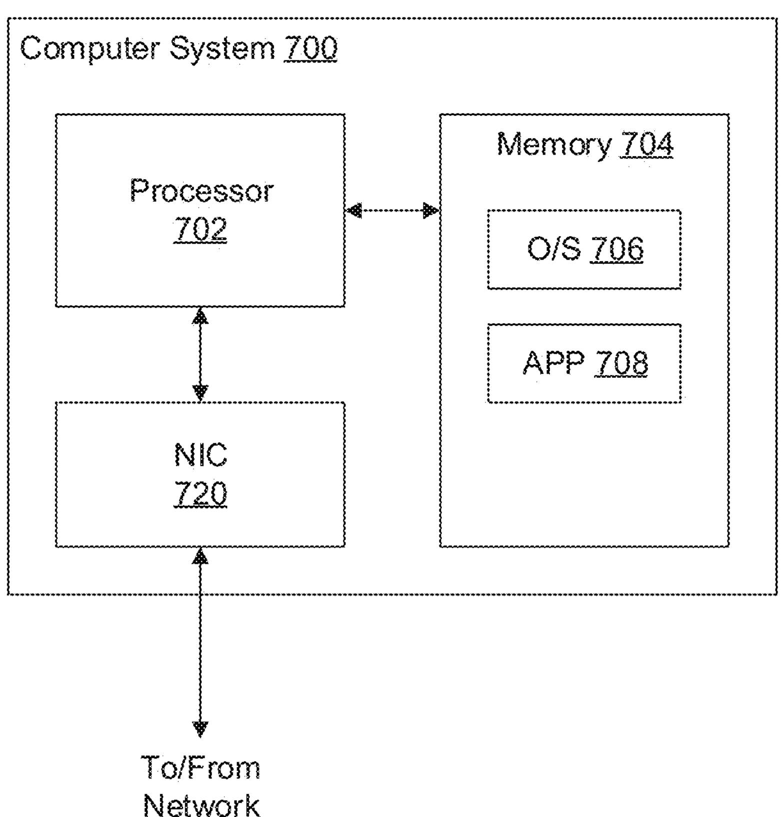
FIG. 7 illustrates an exemplary computer system, in accordance with some examples.

FIG. 7 illustrates an exemplary computer system 700, in accordance with some examples. The computer system 700 includes a processor 702, a non-volatile memory 704, and a network interface controller (NIC) 720. The processor 702 can execute instructions that cause the computer system 700 to implement the functionality various elements of the system 100 described above. For example, the wearable device 180 and/or the server device 110 can each take the form of the computer system 700.

Each of the components 702, 704, and 720 can be interconnected, for example, using a system bus to enable communications between the components. The processor 702 is capable of processing instructions for execution within the system 700. The processor 702 can be a single-threaded processor, a multi-threaded processor, a vector processor or parallel processor that implements a single-instruction, multiple data (SIMD) architecture, or the like. The processor 702 is capable of processing instructions stored in the volatile memory 704. In some examples, the volatile memory 704 is a dynamic random access memory (DRAM). The instructions can be loaded into the volatile memory 704 from a non-volatile storage, such as a Hard Disk Drive (HDD) or a solid state drive (not explicitly shown), or received via the network. In an example, the volatile memory 704 can include instructions for an operating system 706 as well as one or more applications 708. It will be appreciated that the application(s) can be configured to provide the functionality of one or more components of the system 100, as described above. The NIC 720 enables the computer system 700 to communicate with other devices over a network, including a local area network (LAN) or a wide area network (WAN) such as the Internet.

It will be appreciated that the computer system 700 is merely one exemplary computer architecture and that the processing devices implemented in the system 100 can include various modifications such as additional components in lieu of or in addition to the components shown in FIG. 7. For example, in some examples, the computer system 700 can be implemented as a system-on-chip (SoC) that includes a primary integrated circuit die containing one or more CPU cores, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). In another example, the computer system 700 can be implemented as a server device, which can, in some examples, execute a hypervisor and one or more virtual machines that share the hardware resources of the server device.

Figure 8:
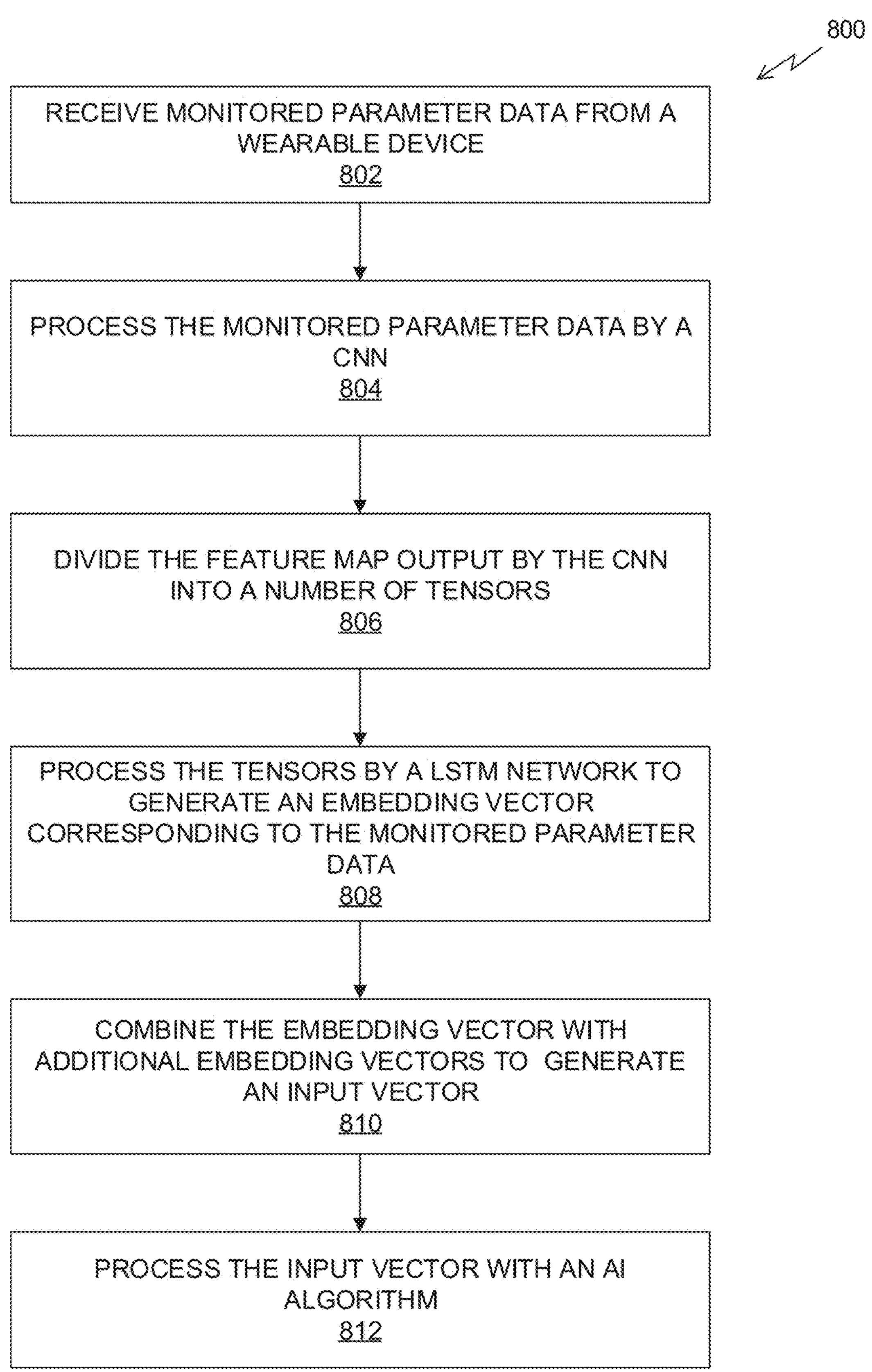
FIG. 8 is a flow diagram of a method for identifying undetected medical conditions based on monitored parameter data collected by a wearable device, in accordance with some examples.

FIG. 8 is a flow diagram of a method 800 for detecting chronic health conditions, in accordance with some examples. The method 800 can be performed by a program, custom circuitry, or by a combination of custom circuitry and a program. Furthermore, persons of ordinary skill in the art will understand that any system that performs method 800 is within the scope and spirit of the examples described herein.

At step 802, monitored parameter data is received from a wearable device. In an example, a server device 110 receives the monitored parameter data from a wearable device 180 via a network 150. The monitored parameter data can include data points (e.g., samples) for one or more monitored parameters that can include at least one of: a heart rate; an oxygen level, an activity level including at least one of a number of steps, a number of flights climbed, or a duration of exercise, or a number of calories burned. In some examples, the monitored parameter data is collected automatically using sensors included in the wearable device 180. In some examples, the monitored parameter data can include manual logged data that is manually entered into the wearable device 180 by a user. Manual logged data can include characteristics such as a height or weight of a user, exercise activity (e.g., a number of minutes for the duration of exercise, a type of exercise, etc.), and the like. In some cases, these characteristics can be automatically logged by the wearable device using sensors or interfaces between the wearable device and other health or fitness equipment. For example, a wearable tracker can establish a communication channel with a smart scale that enables the user's weight to automatically be logged by the wearable tracker every time the user steps on the scale. As another example, the wearable tracker can include inertial sensors that enable the tracker to determine motion consistent with exercise activity and log the number of minutes that the activity is performed.

At step 804, the monitored parameter data is processed by a convolution neural network (CNN) to generate a feature map. In some examples, the CNN includes a plurality of convolutional layers that apply convolution operations to the monitored parameter data. The convolution operations can be one-dimensional convolution operations. In one-dimensional convolution operations, the convolution kernel only slides in one direction, a direction corresponding to time, for example. In an example, the convolution operation is applied sliding along a time axis related to the samples collected on different days and/or multiple samples collected at different times of the same or different days. The CNN generates a feature map related to the monitored parameter data.

At step 806, the feature map is divided into a plurality of tensors, each tensor corresponding to a different day in the number of days. In some examples, the feature map generated by the CNN is processed by a post-processor module that is configured to separate the data into the plurality of tensors associated with different days of, e.g., a seven day window of data collection.

At step 808, the tensors are processed by a long short-term memory (LSTM) network to generate an embedding vector for the monitored parameter data. In some examples, the LSTM network is configured to process each tensor in a time sequential manner, e.g., starting with a tensor corresponding to day d, then a tensor corresponding to day d+1, and so on and so forth. The LSTM generates an embedding vector corresponding to the monitored parameter data.

At step 810, the embedding vector for the monitored parameter data is combined with one or more additional embedding vectors to generate an input vector. In some examples, the embedding vector generated by the LSTM network is concatenated to an embedding network corresponding to the user's health records, such as claims data. The embedding vector may also be added to an additional embedding vector related to social determinants data and/or demographic data for the user; and/or yet another embedding vector related to search terms associated with the user.

At step 812, the input vector is processed by artificial intelligence algorithm to generate an output vector that indicates a prediction related to a plurality of health conditions for a user of the wearable device. In some examples, the artificial intelligence algorithm includes one or more convolutional layers and a plurality of fully connected layers, each fully connected layer corresponding to a particular health condition in the plurality of health conditions. The output of each fully connected layer corresponds to a prediction for a likelihood that the user has a corresponding health condition such as, e.g., diabetes, sleep apnea, hypertension, or the like.

Optionally, the predictions generated by the artificial intelligence algorithm can be used to trigger notifications to be sent to the user or a healthcare professional tasked with treating the user. In an example, a notification message is transmitted to the wearable device to provide a user of the wearable device with a suggested action based on the prediction. The suggested action may help to facilitate making an appointment with a healthcare provider.

It is noted that the techniques described herein may be embodied in executable instructions stored in a computer readable medium for use by or in connection with a processor-based instruction execution machine, system, apparatus, or device. It will be appreciated by those skilled in the art that, for some examples, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described examples. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the examples as claimed.

What is claimed is:

1. A method for detecting health conditions, comprising:

receiving, by a server, monitored parameter data corresponding to data points collected over a number of days from a wearable device associated with a user through a network;

generating, by the server, a plurality of tensors based on applying a convolutional neural network (CNN) to the monitored parameter data, wherein each of the plurality of tensors corresponds to a different day in the number of days;

processing, by the server and in a time sequential manner, the plurality of tensors using a long short-term memory (LSTM) network, wherein processing the plurality of tensors in the time sequential manner corresponds to processing the plurality of tensors in chronological order by the LSTM based on the days corresponding to each tensor;

in response to processing the plurality of tensors, generating, by the server, an embedding vector for the monitored parameter data;

generating, by the server, an output vector that indicates a prediction related to a plurality of health conditions for the user of the wearable device based on using an artificial intelligence algorithm and the embedding vector; and transmitting, by the server and to the user of the wearable device or to a healthcare provider, a notification message that is based on the prediction.

2. The method of claim 1, wherein generating the plurality of tensors based on applying the CNN to the monitor parameter data comprises:

generating a feature map identifying patterns in the monitored parameter data based on applying the CNN to the monitored parameter data; and dividing the feature map into the plurality of tensors.

3. The method of claim 1, wherein generating the output vector that indicates the prediction comprises:

generating an input vector based on combining the embedding vector for the monitored parameter data with one or more additional embedding vectors associated with the user; and generating the output vector based on applying the artificial intelligence algorithm to the input vector.

4. The method of claim 3, wherein the one or more additional embedding vectors comprises a first embedding vector obtained by processing health records for the user via a natural language processing algorithm, wherein the health records correspond to the user of the wearable device.

5. The method of claim 4, wherein the health records are stored in a database and comprise at least one of:

claims records received from a health care provider;

prescription records received from a pharmacy; or laboratory results received from a laboratory or other health care provider.

6. The method of claim 4, wherein the one or more additional embedding vectors further comprises a second embedding vector related to social determinants data comprises one or more of:

economic information;

neighborhood information;

education information;

nutritional information; or other environmental information.

7. The method of claim 6, wherein the second embedding vector is further related to demographic data comprising one or more of:

age information;

gender information;

neighborhood type information;

family size information; or employment indicator information.

8. The method of claim 3, wherein the artificial intelligence algorithm comprises one or more of:

a multi-layer perceptron (MLP) algorithm;

a convolution neural network (CNN); or a recurrent neural network (RNN).

9. The method of claim 3, wherein the artificial intelligence algorithm comprises a number of convolutional layers and a plurality of fully connected layers, each fully connected layer corresponding to a different health condition in the plurality of health conditions.

10. The method of claim 1, wherein the wearable device is an activity tracker, and wherein the monitored parameter data comprises data points related to one or more of:

a heart rate;

an oxygen level;

an activity level comprising at least one of a number of steps, a number of flights climbed, or a duration of exercise; or a number of calories burned.

11. The method of claim 10, wherein the monitored parameter data further comprises information that is logged manually.

12. The method of claim 1, wherein transmitting the notification message comprises transmitting the notification message to one of the wearable device or a mobile device associated with the wearable device to provide the user of the wearable device with a suggested action based on the prediction.

13. The method of claim 12, wherein the suggested action comprises information to facilitate scheduling an appointment with the healthcare provider.

14. A system for detecting health conditions, comprising:

one or more processors; and a non-transitory computer-readable medium having processor-executable instructions stored thereon, wherein the processor-executable instructions, when executed by the one or more processors, facilitate:

receiving monitored parameter data corresponding to data points collected over a number of days from a wearable device associated with a user through a network;

generating a plurality of tensors based on applying a convolutional neural network (CNN) to the monitored parameter data, wherein each of the plurality of tensors corresponds to a different day in the number of days;

processing, in a time sequential manner, the plurality of tensors using a long short-term memory (LSTM) network, wherein processing the plurality of tensors in the time sequential manner corresponds to processing the plurality of tensors in chronological order by the LSTM based on the days corresponding to each tensor;

in response to processing the plurality of tensors, generating an embedding vector for the monitored parameter data;

generating an output vector that indicates a prediction related to a plurality of health conditions for the user of the wearable device based on using an artificial intelligence algorithm and the embedding vector; and transmitting, to the user of the wearable device or to a healthcare provider, a notification message that is based on the prediction.

15. The system of claim 14, wherein generating the plurality of tensors based on applying the CNN to the monitor parameter data comprises:

generating a feature map identifying patterns in the monitored parameter data based on applying the CNN to the monitored parameter data; and dividing the feature map into the plurality of tensors.

16. The system of claim 14, wherein generating the output vector that indicates the prediction comprises:

generating an input vector based on combining the embedding vector for the monitored parameter data with one or more additional embedding vectors associated with the user; and generating the output vector based on applying the artificial intelligence algorithm to the input vector.

17. The system of claim 16, wherein the one or more additional embedding vectors comprises a first embedding vector obtained by processing health records for the user via a natural language processing algorithm, wherein the health records correspond to the user of the wearable device.

18. The system of claim 17, wherein the health records are stored in a database and comprise at least one of:

claims records received from a health care provider;

prescription records received from a pharmacy; or laboratory results received from a laboratory or other health care provider.

19. The system of claim 14, wherein the artificial intelligence algorithm comprises one or more of:

a multi-layer perceptron (MLP) algorithm;

a convolution neural network (CNN); or a recurrent neural network (RNN).

20. A non-transitory computer-readable medium having processor-executable instructions stored thereon, wherein the processor-executable instructions, when executed, facilitate:

receiving monitored parameter data corresponding to data points collected over a number of days from a wearable device associated with a user through a network;

generating a plurality of tensors based on applying a convolutional neural network (CNN) to the monitored parameter data, wherein each of the plurality of tensors corresponds to a different day in the number of days;

processing, in a time sequential manner, the plurality of tensors using a long short-term memory (LSTM) network, wherein processing the plurality of tensors in the time sequential manner corresponds to processing the plurality of tensors in chronological order by the LSTM based on the days corresponding to each tensor;

in response to processing the plurality of tensors, generating an embedding vector for the monitored parameter data;

generating an output vector that indicates a prediction related to a plurality of health conditions for the user of the wearable device based on using an artificial intelligence algorithm and the embedding vector; and transmitting, to the user of the wearable device or to a healthcare provider, a notification message that is based on the prediction.

* * * * *